US010106632B2

(12) United States Patent
Taftaf et al.

(10) Patent No.: US 10,106,632 B2
(45) Date of Patent: Oct. 23, 2018

(54) PROCESS FOR PREPARING A CATALYST COMPONENT FOR POLYMERIZATION OF OLEFINS

(71) Applicants: Mansour Taftaf, Peninsula, OH (US); Jaiprakash Brijlal Sainani, Gujarat (IN); Vladimir Aleksandrovich Zakharov, Geleen (NL); Gennadii Dimitrievich Bukatov, Geleen (NL); Vimalkumar Mahendrabhai Patel, Gujarat (IN); Sergei Andreevich Sergeev, Geleen (NL); Martin Alexander Zuideveld, Kelmis (BE); Aurora Alexandra Batinas-Geurts, Sittard (NL)

(72) Inventors: Mansour Taftaf, Peninsula, OH (US); Jaiprakash Brijlal Sainani, Gujarat (IN); Vladimir Aleksandrovich Zakharov, Geleen (NL); Gennadii Dimitrievich Bukatov, Geleen (NL); Vimalkumar Mahendrabhai Patel, Gujarat (IN); Sergei Andreevich Sergeev, Geleen (NL); Martin Alexander Zuideveld, Kelmis (BE); Aurora Alexandra Batinas-Geurts, Sittard (NL)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/406,124

(22) Filed: Jan. 13, 2017

(65) Prior Publication Data
US 2017/0129974 A1 May 11, 2017

Related U.S. Application Data

(62) Division of application No. 14/762,500, filed as application No. PCT/EP2014/051610 on Jan. 28, 2014, now Pat. No. 9,587,051.

(60) Provisional application No. 61/927,034, filed on Jan. 14, 2014, provisional application No. 61/927,029, filed on Jan. 14, 2014.

(30) Foreign Application Priority Data

Jan. 31, 2013 (EP) .................... 13000481
Jan. 31, 2013 (EP) .................... 13000492
Dec. 20, 2013 (EP) .................... 13199147
Dec. 20, 2013 (EP) .................... 13199160

(51) Int. Cl.
C08F 4/649 (2006.01)
C08F 4/654 (2006.01)
C08F 4/656 (2006.01)
C08F 10/06 (2006.01)
C08F 110/06 (2006.01)
C07C 233/23 (2006.01)
C07C 233/18 (2006.01)
(Continued)

(52) U.S. Cl.
CPC .......... *C08F 110/06* (2013.01); *C07C 233/18* (2013.01); *C07C 233/23* (2013.01); *C07C 233/69* (2013.01); *C08F 4/649* (2013.01); *C08F 4/655* (2013.01); *C08F 4/6546* (2013.01); *C08F 10/06* (2013.01); *C07C 2601/14* (2017.05)

(58) Field of Classification Search
CPC ........ C08F 4/6546; C08F 4/655; C08F 4/656; C08F 4/649
See application file for complete search history.

(56) References Cited

U.S. PATENT DOCUMENTS 6,395,670 B1    5/2002 Morini et al.

FOREIGN PATENT DOCUMENTS

EP    0398698 B1    12/1995
EP    1222214 B1    7/2004
(Continued)

OTHER PUBLICATIONS

International Preliminary Report on Patentability for PCT/EP2014/051610, dated Jun. 16, 2015, 16 pages.
International Search Report for PCT/EP2014/051610 dated Apr. 4, 2014, 4 pages.
Pullukat, Thomas J. and Hoff, Raymond E., "Silica-Based Ziegler-Natta Catalysts: A Patent Review", Catal. Rev.-Sci. Eng., vol. 41 (3 & 4), 389-428 (1999).
(Continued)

*Primary Examiner* — Caixia Lu
(74) *Attorney, Agent, or Firm* — Cantor Colburn LLP

(57) ABSTRACT

The present invention relates to a process for preparing a catalyst component for polymerization of an olefin comprising the steps of: i) contacting a compound $R^9_z MgX_{2-z}$ wherein $R^9$ is aromatic, aliphatic or cyclo-aliphatic group containing up to 20 carbon atoms, X is a halide, and z is in a range of larger than 0 and smaller than 2, with an alkoxy- or aryloxy-containing silane compound to given a first intermediate reaction product; ii) contacting the first intermediate reaction product with at least one activating compound selected from the group formed by electron donors and compounds of formula $M(OR^{10})_{v-w}(OR^{11})_w$, wherein M can be Ti, Zr, Hf, Al or Si, and $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4, and w is smaller than v, to give a second intermediate reaction product; and iii) contacting the second intermediate reaction product with a halogen-containing Ti-compound, a monoester as activating agent, a 1,3-diether as an internal electron donor, and optionally a diester as an additional internal electron donor.

8 Claims, No Drawings

(51) Int. Cl.
*C08F 4/655* (2006.01)
*C07C 233/69* (2006.01)

(56) References Cited

FOREIGN PATENT DOCUMENTS

| EP | 1838741 B1 | 4/2011 |
|----|------------|--------|
| EP | 2027164 B1 | 8/2012 |
| WO | 9632426 A1 | 10/1996 |
| WO | 9957160 A1 | 11/1999 |
| WO | 02100904 A1 | 12/2002 |
| WO | 2004054711 A1 | 7/2004 |
| WO | 2011106497 A1 | 9/2011 |
| WO | 2012017040 A1 | 2/2012 |
| WO | 2014118164 A1 | 8/2014 |
| WO | 2006056338 A1 | 6/2015 |

OTHER PUBLICATIONS

Vaughan, Wyman, et al., "Synthesis of Potential Anticancer Agents, V. Azetidines", Journal of Organic Chemistry. vol. 26, Jan. 1, 1961, pp. 138-144.
Written Opinion of the International Preliminary Examining Authority for PCT/EP2014/051610 dated Dec. 2, 2015, 6 pages.

PROCESS FOR PREPARING A CATALYST COMPONENT FOR POLYMERIZATION OF OLEFINS

This application is a Divisional of U.S. patent application Ser. No. 14/762,500 filed Jul. 22, 2015, entitled "PROCESS FOR PREPARING A CATALYST COMPONENT FOR POLYMERIZATION OF OLEFINS," which is a National Stage filing of International Application No. PCT/EP2014/051610, filed Jan. 28, 2014, which claims priority to U.S. Provisional Application Ser. No. 61/927,029 filed Jan. 14, 2014, U.S. Provisional Application Ser. No. 61/927,034 filed Jan. 14, 2014, European Patent Application 13000481.5 filed Jan. 31, 2013, European Patent Application 13000492.2 filed Jan. 31, 2013, European Patent Application 13199147.3 filed Dec. 20, 2013, and European Patent Application 13199160.6 filed Dec. 20, 2013, which are hereby incorporated by reference in their entirety.

The invention relates to a process for preparing a catalyst component for polymerization of an olefin. Furthermore, the invention relates to catalyst component obtainable by said process. The invention also relates to a process for making a polyolefin by contacting an olefin with a catalyst system containing said catalyst component and to a polyolefin. The invention also directs to use of said catalyst component for polymerization of an olefin.

Document EP2027164B1 discloses a process for preparing a polymerization catalyst component comprising the steps of i) contacting a compound $R^4{}_z MgX_{2-z}$ wherein $R^4$ is an organic group, X is a c, and z is larger than 0 and smaller than 2, with an alkoxy- or aryloxy-containing silane compound to give a solid magnesium-containing compound of formula $Mg(OR^1)_x Cl_{2-x}$ wherein x is larger than 0 and smaller than 2, and each $R^1$, independently, represents an alkyl group; ii) contacting the solid $Mg(OR^1)_x Cl_{2-x}$ with at least one activating compound selected from the group formed by electron donors and compounds of formula $M(OR^2)_{v-w}(R^3)_w$, wherein M can be Ti, Zr, Hf, Al or Si, each $R^2$ and $R^3$, independently, represent an alkyl, alkenyl or aryl group, v is the valency of M and w is smaller than v, in the presence of an inert dispersant to give an intermediate reaction product, and iii) contacting the intermediate reaction product with a halogen-containing Ti-compound and an internal electron donor. The polypropylene obtained by using the catalysts prepared by the process disclosed in EP2027164B1 show limited hydrogen sensitivity.

The 'Ziegler-Natta catalyst' term is well-known in the art and typically refers to catalyst systems comprising a transition metal containing solid catalyst component (also generally referred to in the prior art as procatalyst or catalyst precursor); an organo-metal component as co-catalyst and, optionally, one or more electron donor components (e.g. external donors). The transition metal containing solid catalyst component comprises a transition metal halide, i.e. titanium, chromium, vanadium halide supported on a metal or metalloid compound, such as magnesium chloride or silica. An overview of different catalyst types is for example given by T. Pullukat and R. Hoff in Catal. Rev.—Sci. Eng. 41, vol. 3 and 4, 389-438, 1999.

Other processes to prepare Ziegler-Natta catalyst components suitable for polymerization of olefins are also disclosed in the art. Document WO96/32426A discloses a 3-step process for producing a catalyst for the polymerization of an olefin, wherein in the first two steps a compound $Mg(OAlk)_x Cl_y$ of certain morphology is prepared, and subsequently this solid Mg-compound is contacted with titanium tetrachloride, and an electron-donating compound. EP398698A1 also discloses a process for polymerization of an olefin in the presence of a solid catalyst component, which is obtained by first reacting $Mg(OR^1)_n(OR^2)_{2-n}$, $Ti(OR^3)_4$, $Ti(OAlk)_4$ and $Si(OR^4)_4$ in solution to form an intermediate product, which is further contacted with $TiX_m(OR^6)_{4-m}$ and an electron donating compound EP1838741B1 discloses a process for producing a catalyst for the polymerization of an olefin, wherein a compound with formula $Mg(OAlk)_x Cl_y$, wherein x is larger than 0 and smaller than 2, y equals 2-x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor. Document WO02/100904A1 discloses solid catalyst components comprising Ti, Mg, halogen and an internal electron compound selected from 1,3-diethers. However, the polyolefins obtained by using the catalysts prepared by applying the processes disclosed in these documents show limited hydrogen sensitivity. US6395670B1 discloses catalyst components for the polymerization of olefins having Mg, Ti, halogen and at least two internal electron donor compounds selected from esters containing at least two ether groups and esters of mono or polycarboxylic acids.

There is however an on-going trend in industry towards polymeric materials having high melt flow rates (MFR) which maintain a high stereospecificity. Higher MFR means better processability of the polymer material, i.e. due to good flowability. High MFR of polymers can be obtained by using peroxides during polymer granulating (palletizing). But this leads to narrower MWD of the polymer obtained. Therefore higher MFR values at polymerization are desired. Hydrogen can also be added to polymerization reactors to control MFR values. However, the use of high hydrogen concentration for high MFR is not desirable due to technological problems at polymer, e.g. polypropylene production in commercial reactors. Therefore catalysts with higher hydrogen sensitivity (hydrogen response) providing high MFR at the same hydrogen concentration are important.

Thus, faster throughput of the process for producing end application articles from the polymer, and therefore cost savings, can be achieved. In addition, the xylene solubles, which consist primarily of amorphous (atactic) polymer and oligomers typically increase with increasing MFR, which is not desirable for many applications, for instance in the automotive field and packaging area for food and medicals. Polymers with high stereospecifity are polymers having high isotacticity and thus low amount of atactic polymer fraction. It is already known that the presence of a high atactic fraction in the polymer can deteriorate the properties of the final product, such as decreasing the strength of the materials and also migrating to the material surface causing for instance blooming. Therefore, polymers with high MFR and still high isotacticity, i.e. low atactic polymer content are becoming increasingly important.

It is thus an object of the invention to provide a catalyst for polymerization of an olefin, which allows obtaining polyolefins, especially polypropylene having high melt flow rate and high isotacticity.

This object is achieved with a process for preparing a catalyst component for polymerization of an olefin comprising the steps of:

i) contacting a compound $R^9{}_z MgX_{2-z}$ wherein $R^9$ is aromatic, aliphatic or cyclo-aliphatic group containing up to 20 carbon atoms, X is a halide, and z is in a range of larger than 0 and smaller than 2, with an alkoxy- or aryloxy-containing silane compound to give a first intermediate reaction product;

ii) contacting the first intermediate reaction product with at least one activating compound selected from the group formed by electron donors and compounds of formula $M(OR^{10})_{v-w}(OR^{11})_w$, wherein M can be Ti, Zr, Hf, Al or Si, and $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4, and w is smaller than v, to give a second intermediate reaction product; and iii) contacting the second intermediate reaction product with a halogen-containing Ti-compound, a monoester, a 1,3-diether as an internal electron donor, and optionally, a diester as an additional internal electron donor.

In an embodiment, this object is achieved with a process for preparing a catalyst component for polymerization of an olefin comprising the steps of:

i) contacting a compound $R^9{}_z MgX_{2-z}$ wherein $R^9$ is aromatic, aliphatic or cyclo-aliphatic group containing up to 20 carbon atoms, X is a halide, and z is in a range of larger than 0 and smaller than 2, with an alkoxy- or aryloxy-containing silane compound to give a first intermediate reaction product;

ii) contacting the first intermediate reaction product with at least one activating compound selected from the group formed by compounds of formula $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4, and w is smaller than v, to give a second intermediate reaction product; and iii) contacting the second intermediate reaction product with a halogen-containing Ti-compound, a monoester, a 1,3-diether as an internal electron donor, and optionally, a diester as an additional internal electron donor.

It has been surprisingly found that the process according to the present invention allows preparation of polyolefins, particularly of polypropylenes (PP) having high MFR, for instance higher than 13, 15, 20, 30 or 40 dg/min or even higher than 50 dg/min, and high isotacticity, for instance having an amount of atactic polymer of lower than 3, 2, 1 or 0.6 wt % or even lower than 0.5 wt %.

The key to the present invention is the combination of the use of a monoester—as activator—and a 1,3-diether—as internal donor—during the preparation of a catalyst component. This inventive combination of activator and internal donor leads to a higher yield and a higher melt flow rate, while the molecular weight distribution remains the same or even improves.

A further advantage of the process according to present invention is that low amount of wax is formed, i.e. low molecular weight polymers during the polymerization reaction, which results in reduced or no "stickiness" on the inside walls of the polymerization reactor and inside the reactor. In addition, the catalyst obtained by the process according to the invention has high hydrogen sensitivity. Furthermore, the polyolefins obtained by applying the catalyst obtained by the process according to the present invention have good yield.

SUMMARY OF THE PRESENT INVENTION

In a first aspect, the present invention relates to a process for preparing a catalyst component for polymerization of an olefin comprising the steps of:

contacting a compound $R^9{}_z MgX_{2-z}$ wherein $R^9$ is aromatic, aliphatic or cyclo-aliphatic group containing up to 20 carbon atoms, X is a halide, and z is in a range of larger than 0 and smaller than 2, with an alkoxy- or aryloxy-containing silane compound to give a first intermediate reaction product;

contacting the first intermediate reaction product with at least one activating compound selected from the group formed by electron donors and compounds of formula) $M(OR^{10})_{v-w}(OR^{11})_w$, wherein M can be Ti, Zr, Hf, Al or Si, and $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4, and w is smaller than v; preferably the at least one activation compound is selected from the group formed by compounds of formula $M(OR^{10})_{v-w}(R^{11})_w$, wherein M is Si, to give a second intermediate reaction product; and contacting the second intermediate reaction product with a halogen-containing Ti-compound, a monoester as activating agent, a 1,3-diether as an internal electron donor, and optionally a diester as an additional internal electron donor.

In an embodiment, the 1,3-diether is selected from the group consisting of 1,3-diethers with fluorenyl ligand without or with substituents having C1 to C10 carbon atoms.

In an embodiment, the 1,3-diether is 9,9-bis-methoxymethyl-fluorene.

In another embodiment, the molar ratio between the 1,3-diether of step iii) and Mg is from 0.03 to 0.3.

In another embodiment, the monoester is an ester of an aliphatic monocarboxylic acid with C1-C10 carbon atoms.

In another embodiment, the molar ratio between the monoester in step iii) and Mg is from 0.05 to 0.5.

In another embodiment, the molar ratio between the monoester in step iii) and Mg is from 0.15 to 0.25.

In another embodiment, the diester is a C1-10 aliphatic substituted phthalate.

In another embodiment, the diester is dibutyl phthalate.

In another embodiment, the molar ratio between the diester of step iii) and Mg is from 0.03 to 0.15.

In another embodiment, the second intermediate reaction product is contacted with a halogen-containing Ti-compound and then a monoester is added, then a 1,3-diether as an internal electron donor, and then optionally a diester as an additional internal electron donor is added.

In another aspect, the present invention relates to a catalyst component obtainable by the process according to the present invention comprising Ti, Mg, a halogen, a monoester, a 1,3-diether as an internal electron donor and optionally a diester as an additional internal electron donor, preferably said monoester is present in an amount of less than 4.0 wt. %, more preferably in an amount of at most 3.5 wt. %.

In another aspect, the present invention relates to a catalyst system for polymerization of olefins comprising the catalyst component according to the present invention, a co-catalyst and optionally an external electron donor.

In an embodiment, no external donor is present.

In another aspect, the present invention relates to a process for making a polyolefin by contacting an olefin with the catalyst system comprising a catalyst component prepared by the process for preparing a catalyst component according to the present invention.

In an embodiment, the olefin is propylene.

In another aspect, the present invention relates to the use of a catalyst component prepared by the process for preparing a catalyst component according to the present invention for polymerization of an olefin.

In another aspect, the present invention relates to a polyolefin obtained or obtainable by the process for making a polyolefin according to the present invention.

In an embodiment, said polyolefin is a polypropylene.

In an embodiment, said polyolefin is a homopolymer of propylene.

DETAILED DESCRIPTION OF THE PRESENT INVENTION

The present invention will be described in more detail below.

The process according to the present invention comprises several steps, which are discussed below.

Step i)

In step i) a first intermediate reaction product, i.e. a solid magnesium-containing support is prepared by contacting a compound or a mixture of compounds of formula $R^9_z MgX_{2-z}$ wherein $R^9$ is aromatic, aliphatic or cyclo-aliphatic group containing up to 20 carbon atom, X is a halide, and z is larger than 0 and smaller than 2, with an alkoxy- or aryloxy-containing silane compound, as for example described in WO 96132427 A1 and WO01/23441 A1. In the compound $R^9_z MgX_{2-z}$, also referred to as Grignard compound, X is preferably chlorine or bromine, more preferably chlorine. Preferably, $R^9_z MgX_{2-z}$ is butylmagnesiumchloride or phenylmagnesiumchloride.

Preferably, $R^9$ is aromatic or aliphatic group containing 1 to 20 carbon atoms, preferably 1 to 10 carbon atoms; or cyclo-aliphatic group containing 3 to 20 carbon atoms, preferably 3 to 10 carbon atoms. $R^9$ is more preferably an alkyl, aryl, aralkyl, alkoxide, phenoxide, etc., or mixtures thereof. Most preferably, $R^9$ is methyl, ethyl, n-propyl, i-propyl, n-butyl, i-butyl, t-butyl, hexyl, cyclohexyl, octyl, phenyl, tolyl, xylyl, mesityl or benzyl. In a preferred embodiment of the invention, $R^9$ represents an aromatic group, for instance a phenyl group. The Grignard compound of formula $R^9_z MgX_{2-z}$, wherein z is larger than 0 and smaller than 2, is preferably characterized by z being from about 0.5 to 1.5.

The alkoxy- or aryloxy-containing silane used in step i) is typically a compound or a mixture of compounds with the general formula Si $(OR^{13})_{4-n}R^{14}_n$, wherein n can range from 0 up to 3, preferably n is from 0 up to and including 1, and wherein each $R^{13}$ and $R^{14}$ groups, independently, represent an alkyl, alkenyl or aryl group, optionally containing one or more hetero atoms for instance O, N, S or P, with, for instance, 1-20 C-atoms. Examples of suitable silane-compounds include tetramethoxysilane, tetraethoxysilane, methyltrimethoxysilane, methyltributoxysilane, phenyltriethoxysilane. Preferably, tetraethoxysilane is used as silane-compound in preparing the solid Mg-containing compound in the process according to the invention. Preferably, in step i) the silane-compound and the Grignard compound are introduced simultaneously to a mixing device to result in particles of advantageous morphology, especially of the larger particles, as described in WO 01/23441 A1. Here, 'morphology' does not only refer to the shape of the particles of the solid Mg-compound and the catalyst made therefrom, but also to the particle size distribution (also characterized as span), its fines content, powder flowability, and the bulk density of the catalyst particles. Moreover, it is well known that a polyolefin powder produced in polymerization process using a catalyst system based on such catalyst component has a similar morphology as the catalyst component (the so-called "replica effect"; see for instance S. van der Ven, Polypropylene and other Polyolefins, Elsevier 1990, p. 8-10). Accordingly, almost round polymer particles are obtained with a length/diameter ratio (l/D) smaller than 2 and with good powder flowability. Introduced simultaneously means that the introduction of the Grignard compound and the silane-compound is done in such way that the molar ratio Mg/Si does not substantially vary during the introduction of these compounds to the mixing device, as described in WO 01/23441 A1. The silane-compound and Grignard compound can be continuously or batch-wise introduced to the mixing device. Preferably, the both compounds are introduced continuously to a mixing device.

It is explicitly noted that it is possible that the Grignard compound in step i) may alternatively have a different structure, for example, may be complex. Such complexes are already known to the skilled person in the art; a particular example of such complexes is $Phenyl_4Mg_3Cl_2$.

The mixing device can have various forms; it can be a mixing device in which the silane-compound is premixed with the Grignard compound, the mixing device can also be a stirred reactor, in which the reaction between the compounds takes place. Preferably, the compounds are premixed before the mixture is introduced to the reactor for step i). In this way, a catalyst component is formed with a morphology that leads to polymer particles with the best morphology (high bulk density, narrow particle size distribution, (virtually) no fines, excellent flowability). The Si/Mg molar ratio during step i) may vary within wide limits for instance from 0.2 to 20. Preferably, the Si/Mg molar ratio is from 0.4 to 1.0.

The period of premixing in above indicated reaction step may vary between wide limits, for instance 0.1 to 300 seconds. Preferably premixing is performed during 1 to 50 seconds.

The temperature during the premixing step is not specifically critical, and may for instance range between 0 and 80° C.; preferably the temperature is between 10° C. and 50° C. The reaction between said compounds may, for instance, take place at a temperature between −20° C. and 100° C.; preferably at a temperature of from 0° C. to 80° C.

The first intermediate reaction product obtained from the reaction between the silane compound and the Grignard compound is usually purified by rinsing with an inert solvent, for instance a hydrocarbon solvent with for example 1-20 C-atoms, like pentane, iso-pentane, hexane or heptane. The solid product can be stored and further used as a suspension in said inert solvent. Alternatively, the product may be dried, preferably partly dried, and preferably under mild conditions; e.g. at ambient temperature and pressure.

The first intermediate reaction product obtained by this step i) may comprise a compound of the formula $Mg(OR^{13})_x X_{2-x}$, wherein the group $R^{13}$ is an alkyl containing 1-12 carbon atoms or an aryl group containing 3-12 carbon atoms, although the present invention is not limited thereby. X is a halide, and x is larger than 0 and smaller than 2, preferably between 0.5 and 1.5. Preferably, X is chlorine or bromine and more preferably, X is chlorine.

Preferably, the $R^{13}$ group contains 1-8 carbon atoms. More preferably, at least one of the $R^{13}$ groups represents an ethyl group. In a preferred embodiment, each $R^{13}$ group represents an ethyl group.

$R^9_z MgX_{2-z}$ used in step i) may be prepared by contacting metallic magnesium with an organic halide $R^9X$, as described in WO 96/32427 A1 and WO01/23441 A1. All forms of metallic magnesium may be used, but preferably use is made of finely divided metallic magnesium, for example magnesium powder. To obtain a fast reaction it is preferable to heat the magnesium under nitrogen prior to use. $R^9$ and X have the same meaning as described above. Combinations of two or more organic halides $R^9X$ can also be used.

The magnesium and the organic halide $R^9X$ can be reacted with each other without the use of a separate dispersant; the organic halide $R^9X$ is then used in excess. The organic halide $R^9X$ and the magnesium can also be brought into contact with one another and an inert dispersant. Examples of these dispersants are: aliphatic, alicyclic or aromatic dispersants containing from 4 up to 20 carbon atoms.

In this step of preparing $R^9_zMgX_{2-z}$, also an ether can be added to the reaction mixture. Examples of suitable ethers are: diethyl ether, diisopropyl ether, dibutyl ether, diisobutyl ether, diisoamyl ether, diallyl ether, tetrahydrofuran and anisole. Dibutyl ether and/or diisoamyl ether are preferably used. Preferably, an excess of chlorobenzene is used as the organic halide $R^9X$. Thus, the chlorobenzene serves as dispersant as well as organic halide $R^9X$.

The organic halide/ether ratio acts upon the activity of the catalyst component. The chlorobenzene/dibutyl ether volume ratio may for example vary between 75:25 and 35:65, preferably between 70:30 and 50:50.

Small amounts of iodine and/or alkyl halides can be added to cause the reaction between the metallic magnesium and the organic halide $R^9X$ to proceed at a higher rate. Examples of alkyl halides are butyl chloride, butyl bromide and 1,2-dibromoethane. When the organic halide $R_9X$ is an alkyl halide, iodine and 1,2-dibromoethane are preferably used.

The reaction temperature for preparing $R^9_zMgX_{2-z}$ normally is between 20 and 150° C.; the reaction time is normally between 0.5 and 20 hours. After the reaction for preparing $R^9_zMgX_{2-z}$, is completed, the dissolved reaction product may be separated from the solid residual products.

Step ii)

The first intermediate reaction product is contacted in step ii) with at least one activating compound selected from the group formed by electron donors and compounds of formula $M(OR^{10})_{v-w}(OR^{11})_w$, wherein M can be Ti, Zr, Hf, Al or Si, and $M(OR^{10})_{v-w}(R^{11})_w$, wherein M is Si, each $R^{10}$ and $R^{11}$, independently, represent an alkyl, alkenyl or aryl group, v is the valency of M, being either 3 or 4, and w is smaller than v.

In an embodiment, the first intermediate reaction product is contacted in step ii) with at least one activating compound selected from the group formed by compounds of formula $M(OR^{10})_{v-w}(R^{11})_w$, wherein M is Si, each $R^{10}$ and $R^{11}$, independently, represent an alkyl, alkenyl or aryl group, v is the valency of M, being either 3 or 4, and w is smaller than v.

The electron donor and the compound of formula $M(OR^{10})_{v-w}(OR^{11})_w$ and $M(OR^{10})_{v-w}(R^{11})_w$ may be also referred herewith as activating compounds.

Examples of suitable electron donors that can be used in step ii) are known to the skilled person in the art and include alcohols, carboxylic acids and carboxylic acid derivatives. Preferably, an alcohol is used as the electron donor in step ii). More preferably, the alcohol is a linear or branched aliphatic or aromatic having 1-12 carbon atoms. Even more preferably, the alcohol is selected from methanol, ethanol, butanol, isobutanol, hexanol, xylenol and benzyl alcohol. Most preferably, the alcohol is ethanol or methanol.

Examples of suitable carboxylic acids include formic acid, acetic acid, propionic acid, butyric acid, isobutanoic acid, acrylic acid, methacrylic acid, maleic acid, fumaric acid, tartaric acid, cyclohexanoic monocarboxylic acid, cis-1,2-cyclohexanoic dicarboxylic acid, phenylcarboxylic acid, toluenecarboxylic acid, naphthalene carboxylic acid, phthalic acid, isophthalic acid, terephthalic acid and/or trimellitic acid.

$R^{10}$ and $R^{11}$ groups can be a linear, branched or cyclic alkyl or alkenyl group, suitable groups containing up to 20 carbon atoms, preferably 1-12 or 1-8 carbon atoms; in case of cyclic alkyl groups, $R^{10}$ and $R^{11}$ groups preferably have at least 3 carbon atoms; preferably 3-12 or 3-8 carbon atoms. The groups may differ independently or be the same. Preferably, at least one of the $R^{10}$ groups represents an ethyl group. In preferred embodiments, $R^{10}$ and $R^{11}$ are ethyl, propyl or butyl; more preferably, all groups are ethyl groups. $R^{10}$ and $R^{11}$ can also be aromatic hydrocarbon groups, optionally substituted with e.g. alkyl groups and can contain for example from 6 to 20 carbon atoms.

Preferably, M in said activating compound is Ti or Si. Preferably, the value of w is 0, the activating compound being for example a titanium tetraalkoxide containing 4-32 C-atoms. The four alkoxide groups in the compound may be the same or may differ independently. Preferably, at least one of the alkoxy groups in the compound is an ethoxy group. More preferably the compound is a tetraalkoxide, like titanium tetraethoxide. Si-containing compounds suitable as activating compounds are the same as listed above for step i).

Preferably, a Ti-based compound, for example titanium tetraethoxide, is used together with an alcohol, like ethanol or methanol in step ii) to give the second intermediate reaction product.

If two or more compounds are used in step ii) of the preferred process according to the invention, their order of addition is not critical, but may affect catalyst performance depending on the compounds used. A skilled person may optimize their addition based on some experiments. The compounds of step ii) can be added together or sequentially.

The first intermediate reaction product can be contacted in any sequence with at least one activating compound selected from the group formed by electron donors and compounds of formula $M(OR^{10})_{v-w}(OR^{11})_w$ and $M(OR^{10})_{v-w}(R^{11})_w$. Preferably, the electron donor is first added to the first intermediate reaction product and then the compound $M(OR^{10})_{v-w}(OR^{11})_w$ or $M(OR^{10})_{v-w}(R^{11})_w$ is added; in this order no agglomeration of solid particles is observed. The compounds in step ii) are preferably added slowly, for instance during a period of 0.1-6, preferably during 0.5-4 hours, most preferably during 1-2.5 hours, each.

The first intermediate reaction product and the electron donor and/or the compound of formula $M(OR^{10})_{v-w}(OR^{11})_w$ or $M(OR^{10})_{v-w}(R^{11})_w$ may be contacted with an inert dispersant in step ii). The dispersant is preferably chosen such that virtually all side products are dissolved in the dispersant and/or to act as an inert diluent for the Mg-containing support particles. Any substance known in the art that is inert to the Mg-containing support particles may be used as inert dispersant. The dispersant may be an aromatic or aliphatic hydrocarbon compound. The inert dispersant is preferably a hydrocarbon solvent and more preferably it is selected from the groups of linear and branched aliphatic and aromatic hydrocarbon compounds with, for instance, 4-20 C-atoms. Suitable dispersants include for example aliphatic and aromatic hydrocarbons and halogenated aromatic solvents with for instance 4-20 C-atoms; alkyl and aryl halides; ethers. Preferably, the dispersant is an aliphatic hydrocarbon, more preferably pentane, iso-pentane, hexane or heptane, heptane being most preferred.

The molar ratio of the activating compound to the magnesium atom of the first intermediate reaction product may range between wide limits and is, for instance, between 0.02 and 1.0. Preferably the molar ratio is between 0.1 and 0.7, depending on the type of activating compound, in the process according to the invention, the temperature in step ii) can be in the range from −20° C. to 70° C., preferably from −10° C. to 50° C., more preferably in the range between 0° C. and 30° C. Preferably, at least one of the reaction components is dosed in time, for Instance during 0.1 to 6, preferably during 0.5 to 4 hours, more particularly during 1-2.5 hours.

The obtained second intermediate reaction product is typically a solid and may be further washed, preferably with the solvent also used as inert dispersant; and then stored and further used as a suspension in said inert solvent. Alternatively, the product may be dried, preferably partly dried, preferably slowly and under mild conditions; e.g. at ambient temperature and pressure.

Starting from a solid Mg-containing product of controlled morphology, said morphology is not negatively affected during treatment with the activating compound. The solid second intermediate reaction product obtained is considered to be an adduct of the Mg-containing compound and the at least one compound as defined in step ii), and is still of controlled morphology. This second intermediate reaction product can be also referred herein as solid catalyst support containing magnesium.

Preferably, the solid first intermediate reaction product is contacted with an alcohol and then with a titanium tetraalkoxide and optionally an inert dispersant to give a solid second intermediate reaction product, which is further applied in step iii).

Step iii)

Preferably, step iii) is carried out by contacting the second intermediate reaction product with a halogen-containing Ti-compound and a monoester and then adding a 1,3-diether as an internal electron donor, and optionally, a diester as an additional internal electron donor, to provide higher catalyst stereospecificity, high MFR and control the polypropylene molecular structure.

An internal electron donor (also referred to as internal donor) is herein defined as an electron-donating compound that is commonly described in prior art as a reactant in the preparation of a solid catalyst component for a Ziegler-Natta catalyst system for an olefin polymerization; i.e. contacting a magnesium-containing support with a halogen-containing Ti compound and an internal donor.

The Ti/Mg molar ratio in the reaction between the second intermediate reaction product and halogen-containing titanium compound preferably is between 10 and 100, most preferably, between 10 and 50. Titanium tetrachloride is the most preferred halogen-containing titanium compound.

The internal electron donor in step iii) (also referred herein as the first internal electron donor) can be any 1,3-diether known in the art, such as C6-C20 aromatic and C1-C20 aliphatic substituted 1,3-diethers and preferably, C10-C30, preferably C12-C20 polycyclic aromatic hydrocarbons. Preferably, the 1,3-diether is 2,2-diisobutyl-1,3-dimethoxypropane, 2,2-dicyclopentyl-1,3-dimethoxypropane, 2-ethyl-2-butyl-1,3-dimethoxypropane, 2-isopropyl-2-isopentyl-1,3-dimethoxypropane, 1,1-bis(methoxymethyl)-cyclopentadiene, 1,1-bis(methoxymethyl)-2,3,4,5-tetramethylcyclopentadiene; 1,1-bis(methoxymethyl)-2,3,4,5-tetraphenylcyclopentadiene; 1,1-bis(methoxymethyl)indene; 1,1-bis(methoxymethyl)-2,3-dimethylindene; 1,1-bis(methoxymethyl)-cyclopenthylindene; 9,9-bis(methoxymethyl) fluorene; 9,9-bis(methoxymethyl)-2,3,6,7-tetramethylfluorene; 9,9-bis(methoxymethyl)-2,3-benzofluorene; 9,9-bis(methoxymethyl)-2,7-diisopropylfluorene; 9,9-bis(methoxymethyl)-1,8-dichlorofluorene; 9,9-bis(methoxymethyl)-2,7-dicyclopentylfluorene; 9,9-bis(methoxymethyl)difluorofluorene; 9,9-bis(methoxymethyl)-1,2,3,4-tertrahydrofluorene; and 9,9-bis(methoxymethyl)-4-tert-butylfluorene are used as an internal electron donor. More preferably, the internal electron donor in step iii) is selected from the group consisting of 1,3-diethers with fluorenyl ligand without or with substitutents having C1 to C10 carbon atoms for providing the higher hydrogen sensitivity. Most preferably, the internal electron donor is 9,9-bis-methoxymethyl-fluorene.

The molar ratio between the 1,3-diether and Mg may range from 0.03 to 0.3, preferably from 0.04 to 0.2, and more preferably from 0.05 to 0.1.

The monoester according to the present invention can be any ester of a monocarboxylic acid known in the art. The monoester can have the formula R'—CO—OR", wherein R' can be the same or different from R".

R' and R" may be selected from the group consisting of hydrogen, straight, branched and cyclic alkyl having at most 20 carbon atoms and aromatic substituted and unsubstituted hydrocarbyl having 6 to 20 carbon atoms. Particularly, R' may be selected from the group consisting of hydrogen; straight and branched alkyl having 1 to 20 carbon atoms, preferably 1 to 10 carbon atoms and most preferably 1 to 5 carbon atoms; and cyclic alkyl having 3 to 20 carbon atoms, preferably 3 to 10 carbon atoms and most preferably 3 to 5 carbon atoms; and aromatic substituted and unsubstituted hydrocarbyl having 6 to 20 carbon atoms, preferably 6 to 10 carbon atoms.

Suitable examples of monoesters include formates, for instance, butyl formate; acetates, for instance ethyl acetate, amyl acetate and butyl acetate; acrylates, for instance ethyl acrylate, methyl methacrylate and isobutyl methacrylate; benzoates, particularly C1-C20 hydrocarbyl esters of benzoic acid, wherein the hydrocarbyl group is substituted or unsubstituted with one or more Group 14, 15 or 16 heteroatom containing substituents and C1-C20 (poly)hydrocarbyl ether derivatives thereof, preferably, C1-C4 alkyl benzoate and C1-C4 ring alkylated derivatives thereof; more preferably, methyl benzoate, ethyl benzoate, propyl benzoate, methyl p-methoxy benzoate, methyl p-ethoxy benzoate; most preferably ethyl benzoate. Other suitable examples include methyl-p-toluate and ethyl-naphthate. More preferably, the monoester is an acetate or a benzoate. Most preferably, the monoester is ethyl acetate, amyl acetate or ethyl benzoate.

Most preferably, the monoester used in step iii) is an ester of an aliphatic monocarboxylic acid having C1-C10 carbon atoms.

The molar ratio between the monoester in step iii) and Mg may range from 0.05 to 0.5, preferably from 0.1 to 0.4, and most preferably from 0.15 to 0.25.

In an embodiment, the amount of monoester is less than 4 wt. % based on the total weight of the catalyst component, preferably the amount of monoester is at most 3.5 wt. %. In an embodiment, the amount of monoester is at least 2.5 wt. %. This amount is sufficiently low to ensure that the monoester will only react as activator and (hardly) not as internal donor. The effect on the selectivity of the 1,3-diether as internal donor is hence remained without any significant effect of the monoester also acting as internal donor.

The monoester in step iii) of the present invention is not a stereospecificity agent, like usual internal donors are known to be in the prior art. Without to be bound by any theory, the inventors believe that the monoester used in the process according to the present invention participates at the formation of the magnesium halogen (e.g. $MgCl_2$) crystallites during the Interaction of Mg-containing support with titanium halogen (e.g. $TiCl_4$). The monoester may form intermediate complexes with Ti and Mg halogen compounds (for instance, $TiCl_4$, $TiCl_3(OR)$, $MgCl_2$, $MgCl(OEt)$, etc.), help to the removal of titanium products from solid particles to mother liquor and affect the activity of final catalyst. Therefore, the monoester according to the present invention can also be referred to as an activating agent.

The diester (also referred herein as the second internal electron donor) can be any diester of a C6-C20 aromatic and C1-C20 aliphatic dicarboxylic acid known in the art. Suitable examples of diesters include C6-C20 aromatic or a C1-C20 aliphatic substituted phthalates, e.g. dibutyl phthalate, diisobutyl phthalate, diallyl phthalate and/or diphenyl phthalate; C6-C20 aromatic or a C1-C20 aliphatic substituted succinates; and also C6-C20 aromatic or a C1-C20 aliphatic substituted esters of malonic acid or glutaric acid. Preferably the diester is a C1-010 aliphatic substituted phthalate, more preferably dibutyl phthalate.

The molar ratio between the diester of step iii) and Mg may range from 0.03 to 0.15, preferably from 0.05 to 0.1.

The second intermediate reaction product can be contacted with the halogen-containing Ti-compound, the monoester, the 1,3-diether and optionally the diester at any time and any stage and by applying any method known to the skilled person in the art.

Preferably, at first the second intermediate reaction product is contacted with the halogen-containing Ti-compound and then the monoester is added to the reaction (may be also referred herein as stage I of titanation reaction) and then the 1,3-diether is added to the reaction (may be also referred herein as stage II or III of titanation reaction) and then optionally the diester is added to the reaction.

Particularly, in step iii) the second intermediate reaction product may be contacted with titanium tetrachloride and the monoester at a reaction temperature that may be between 80° C. and 130° C., preferably 90 and 120° C. and a reaction time that may be 50 to 150 min, preferably for 90 to 110 min (stage I of reaction). After a purification step (such as separation and washing), a halogen-containing titanium compound may be added to the product of stage I and the reaction may be kept at a temperature of between 80 and 120° C. for preferably 20 to 60 min (stage II of reaction). Stage II may be repeated once (stage III of reaction). The 1,3-diether may be added after the monoester and preferably, the 1,3-diether is added in stage III or I when the diester is not added or in stage II when the diester is added. The diester is more preferably added in stage III of the reaction. Chlorobenzene may be used as the effective solvent for the removal of titanation products (e.g. $TiCl_n(OEt)_{4-n}$) and their complexes with donors from solid particles to mother liquor.

The reaction temperature during contacting in step iii) the second intermediate reaction product and the halogen-containing titanium compound may be preferably between 0° C. and 150° C., more preferably between 50° C. and 150° C., and more preferably between 80° C. and 130° C. Most preferably, the reaction temperature is between 90° C. and 120° C. The contacting time between the components in step iii) may be between 10 and 200 min, preferably between 30 and 120 min. During the titanation reaction an inert aliphatic or aromatic hydrocarbon or halogenated aromatic compound can be used. If desired, the reaction and subsequent purification steps may be repeated one or more times. A final washing is preferably performed with an aliphatic hydrocarbon to result in a suspended or at least partly dried catalyst component, as described above for the other steps.

The invention further relates to a catalyst component for polymerization of an olefin obtainable by the process according to the invention. This catalyst component comprises Ti, Mg, a halogen, a monoester, a 1,3-diether as an internal electron donor, and optionally a diester as an additional internal electron donor. Particularly, said catalyst component comprises a magnesium-containing support, a halogen-containing titanium compound, a monoester as activating agent, a 1,3-diether as an internal electron donor, and optionally a diester as an additional internal electron donor. All these components are as defined herein. More preferably, the catalyst component according to the present invention comprises a magnesium dichloride, titanium tetrachloride, a monoester as activating agent, a 1,3-diether and optionally a diester as internal electron donors. By applying said catalyst obtainable with the process, higher MFRs and high isotacticity of the polyolefins are obtained.

The invention also relates to the use of the monoester as activating agent in a catalyst component for polymerization of an olefin.

The term "catalyst component" may be also referred herein to as "procatalyst" or "solid catalyst component" or "catalyst precursor".

The invention also relates to a catalyst system for polymerization of an olefin that comprises the catalyst component according to the invention and a co-catalyst. Preferably, the catalyst system also comprises an external electron-donating compound, also referred to as external electron donor, or simply external donor. The main function of this external donor compound is to affect the stereoselectivity of the catalyst system in polymerization of an olefin having 3 or more carbon atoms, and therefore it may be also referred to as selectivity control agent.

The invention further relates to a process of making a polyolefin by contacting at least one olefin with a polymerization catalyst system comprising the catalyst component according to the present invention.

Preferably, the polyolefin made by using the catalyst system of the present invention is polypropylene. It is an advantage of the present invention that polypropylene obtainable by employing said catalyst has higher MFR, low atactic polymer fraction and high isotacticity.

The preparation of polyolefins may take place by polymerizing an olefin, i.e. one or more olefins simultaneously and/or successively in the presence of a catalyst system comprising the catalyst component obtainable by the process according to the invention, a co-catalyst and optionally an external donor. The olefin according to the invention may be selected from mono- and di-olefins containing from 2 to 10 carbon atoms, such as for example ethylene, propylene, butylene, hexene, octene and/or butadiene. According to a preferred embodiment of the invention the olefin is propylene or a mixture of propylene and ethylene, to result in a propylene homopolymer or copolymer. The present invention includes in one aspect a polyolefin obtained or obtainable by a process for making a polyolefin according to the present invention, preferably said polyolefin is a polypropylene, more preferably a homopolymer of propylene. A propylene copolymer is herein meant to include both so-called random copolymers with relatively low comonomer content, e.g. up to 10 mol %, as well as so-called impact, also known as heterophasic or block propylene copolymers comprising higher comonomer contents, e.g. from 5 to 80 mol %, more typically from 10 to 60 mol %. The impact copolymers are actually blends of different propylene polymers; such copolymers can be made in one or two reactors and can be blends of a first component of low comonomer content and high crystallinity, and a second component of high comonomer content having low crystallinity or even rubbery properties. Such random and impact copolymers are well-known to the skilled person in the art.

Preferably, the co-catalyst is an organometallic compound containing a metal from group 1, 2, 12 or 13 of the Periodic System of the Elements (Handbook of Chemistry and Physics, 70th Edition, CRC Press, 1989-1990), wherein the system further comprises an external electron donor. Preferably, the co-catalyst is an organoaluminum compound. The organoaluminum compound may be, for instance, a compound having the formula $AlR^{15}_3$, wherein each $R^{15}$ independently represents an alkyl group with, for instance, 1-10 C-atoms or an aryl group with, for instance, 6-20 C-atoms. Examples of a suitable organoaluminum compound are trimethylaluminium, triethylaluminium, triisobutylaiuminium, and/or trioctylaiuminium. Preferably, the co-catalyst is triethylaluminium.

The molar ratio of the metal of the co-catalyst relative to titanium in the polymerization catalyst system during the polymerization may vary for instance from 5 to 2000. Preferably, this ratio is between 50 and 300.

Examples of suitable external donors include organo-silicon compounds. Mixtures of external donors can also be used. Examples of organo-silicon compounds that are suitable as external donor are compounds or mixtures of compounds of general formula $Si(OR^{16})_{4-n}R^{17}_n$, wherein n can be from 0 up to 2 preferably n is 1 or 2 as higher values have no positive effect on stereospecificity, and each $R^{16}$ and $R^{17}$, independently, represents an alkyl or aryl group, optionally containing one or more hetero atoms for instance O, N, S or P, with, for instance, 1-20 C-atoms, as defined above for $R^{13}$ and $R^{14}$. Examples of suitable compounds include the silane-compounds that can be used at step i), as described above. Preferably the organo-silicon compound used as external donor is n-propyl trimethoxysilane.

The aluminium/external donor molar ratio in the polymerization catalyst system preferably is between 1 (if less than 1 no polymerization occurs) and 200; more preferably between 5 and 100.

Preferably, no external donor is used in said catalyst system as polymers having high MFR (e.g. higher than 20 dg/min or higher than 40 dg/min or even higher than 50 dg/min) and also low amount of atactic polymers and relatively low XS are obtained. It is an additional economic advantage of the present invention that the use of an external donor can be avoided.

The polymerization process can be carried out in the gas phase or in the liquid phase (in bulk or slurry). In the case of polymerization in a slurry (liquid phase) a diluent may be present. Suitable diluents include for example n-butane, isobutane, n-pentane, isopentane, hexane, heptane, octane, cyclohexane, benzene, toluene, xylene and liquid propylene. The polymerization conditions of the process according to the invention, such as for example the polymerization temperature and time, monomer pressure, avoidance of contamination of catalyst, choice of polymerization medium in slurry processes, the use of further ingredients (like hydrogen) to control polymer molar mass, and other conditions are well known to persons of skill in the art. The polymerization temperature may vary within wide limits and is, for example for propylene polymerization, between 0° C. and 120° C., preferably between 40° C. and 100° C. The pressure during (propylene) (co)polymerization is for instance between 0.1 and 6 MPa, preferably between 0.5-3 MPa.

The molar mass of the polyolefin obtained during the polymerization can be controlled by adding during the polymerization hydrogen or any other agent known to be suitable for the purpose. The polymerization can be carried out in a continuous mode or batch-wise. Slurry-, bulk-, and gas-phase polymerization processes, multistage processes of each of these types of polymerization processes, or combinations of the different types of polymerization processes in a multistage process are contemplated herein. Preferably the polymerization process is a single stage gas phase process or a multistage, for instance a 2-stage, gas phase process wherein in each stage a gas-phase process is used.

Examples of gas-phase polymerization processes include both stirred bed reactors and fluidized bed reactor systems; such processes are well known in the art. Typical gas phase α-olefin polymerization reactor systems comprise a reactor vessel to which alpha-olefin monomer(s) and a catalyst system can be added and which contain an agitated bed of growing polymer particles.

The present invention further relates to the use of the catalyst component obtainable by the process according to the present invention for polymerization of an olefin. Polyolefins with high MFR, high isotacticity and low amount of atactic polymer fraction are produced by using said catalyst.

It is noted that the invention relates to all possible combinations of features recited in the claims. Features described in the description may further be combined.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will be further elucidated with the following examples without being limited hereto.

EXAMPLES

Example 1

A. Grignard Formation Step

This step was carried out as described in Example XVI of EP 1 222 214 B1.

A stainless steel reactor of 9 l volume was filled with magnesium powder 360 g. The reactor was brought under nitrogen. The magnesium was heated at 80° C. for 1 hour, after which a mixture of dibutyl ether (1 liter) and chlorobenzene (200 ml) was added. Then iodine (0.5 g) and n-chlorobutane (50 ml) were successively added to the reaction mixture. After the colour of the iodine had disappeared, the temperature was raised to 94° C. Then a mixture of dibutyl ether (1.6 liter) and chlorobenzene (400 ml) was slowly added for 1 hour, and then 4 liter of chlorobenzene was slowly added for 2.0 hours. The temperature of reaction mixture was kept in Interval 98-105° C. The reaction mixture was stirred for another 6 hours at 97-102° C. Then the stirring and heating were stopped and the solid material was allowed to settle for 48 hours. By decanting the solution above the precipitate, a solution of phenylmagnesiumchloride reaction product A has been obtained with a concentration of 1.3 mol Mg/l. This solution was used in the further catalyst preparation.

B. Preparation of the First Intermediate Reaction Product

This step was carried out as described in Example XX of EP 1 222 214 B1, except that the dosing temperature of the reactor was 35° C., the dosing time was 360 min and the propeller stirrer was used. 250 ml of dibutyl ether was introduced to a 1 liter reactor. The reactor was fitted by propeller stirrer and two baffles. The reactor was thermostated at 35° C.

The solution of reaction product of step A (360 ml, 0.488 mol Mg) and 180 ml of a solution of tetraethoxysilane (TES) in dibutyl ether (DBE), (55 ml of TES and 125 ml of DBE), were cooled to 10° C., and then were dosed simultaneously to a mixing device of 0.45 ml volume supplied with a stirrer and jacket. Dosing time was 360 min. Thereafter the pre-mixed reaction product A and the TES-solution were introduced to a reactor. The mixing device (minimixer) was cooled to 10° C. by means of cold water circulating in the minimixer's jacket. The stirring speed in the minimixer was 1000 rpm. The stirring speed in reactor was 350 rpm at the beginning of dosing and was gradually increased up to 600 rpm at the end of dosing stage.

On the dosing completion the reaction mixture was heated up to 60° C. and kept at this temperature for 1 hour. Then the stirring was stopped and the solid substance was allowed to settle. The supernatant was removed by decanting. The solid substance was washed three times using 500 ml of heptane. As a result, a pale yellow solid substance, reaction product B (the solid first intermediate reaction product; the support), was obtained, suspended in 200 ml of heptane. The average particle size of support was 22 μm and span value $(d_{90}-d_{10})/d_{50}=0.5$.

C. Preparation of the Second Intermediate Reaction Product

Support activation was carried out as described in Example VIII of EP 2027164B1 to obtain the second intermediate reaction product.

In inert nitrogen atmosphere at 20° C. a 250 ml glass flask equipped with a mechanical agitator is filled with slurry of 5 g of reaction product B dispersed in 60 ml of heptane. Subsequently a solution of 0.22 ml ethanol (EtOH/Mg=0.1) in 20 ml heptane is dosed under stirring during 1 hour. After keeping the reaction mixture at 20° C. for 30 minutes, a solution of 0.79 ml titanium tetraethoxide (TET/Mg=0.1) in 20 ml of heptane was added for 1 hour.

The slurry was slowly allowed to warm up to 30° C. for 90 min and kept at that temperature for another 2 hours. Finally the supernatant liquid is decanted from the solid reaction product (the second intermediate reaction product; activated support) which was washed once with 90 ml of heptane at 30° C.

D. Preparation of the Catalyst Component

A reactor was brought under nitrogen and 125 ml of titanium tetrachloride was added to it. The reactor was heated to 90° C. and a suspension, containing about 5.5 g of activated support in 15 ml of heptane, was added to it under stirring. The reaction mixture was kept at 90° C. for 10 min. Then add 0.866 g of ethyl acetate (EA/Mg=0.25 molar ratio). The reaction mixture was kept for 60 min (stage I of catalyst preparation). Then the stirring was stopped and the solid substance was allowed to settle. The supernatant was removed by decanting, after which the solid product was washed with chlorobenzene (125 ml) at 90° C. for 20 min.

The washing solution was removed by decanting, after which a mixture of titanium tetrachloride (62.5 ml) and chlorobenzene (62.5 ml) was added. The reaction mixture was kept at 90° C. for 30 min (stage II of catalyst preparation). After which the stirring was stopped and the solid substance was allowed to settle. The supernatant was removed by decanting, after which a mixture of titanium tetrachloride (62.5 ml) and chlorobenzene (62.5 ml) was added. Then 0.5 g of 9,9-bis-methoxymethyl-fluorene (flu) (flu/Mg=0.05 molar ratio) in 3 ml of chlorobenzene was added to reactor and the temperature of reaction mixture was increased to 115° C. The reaction mixture was kept at 115° C. for 30 min (stage III of catalyst preparation). After which the stirring was stopped and the solid substance was allowed to settle. The supernatant was removed by decanting, after which a mixture of titanium tetrachloride (62.5 ml) and chlorobenzene (62.5 ml) was added. The reaction mixture was kept at 115° C. for 30 min (stage IV of catalyst preparation), after which the solid substance was allowed to settle. The supernatant was removed by decanting and the solid was washed five times using 150 ml of heptane at 60° C., after which the catalyst component, suspended in heptane, was obtained.

E. Polymerization of Propylene

Polymerization of propylene was carried out in a stainless steel reactor (with a volume of 0.7 l) in heptane (300 ml) at a temperature of 70° C., total pressure 0.7 MPa and hydrogen presence (55 ml) for 1 hour in the presence of a catalyst system comprising the catalyst component according to step D, triethylaluminum and n-propyltrimethoxysilane. The concentration of the catalyst component was 0.033 g/l; the concentration of triethylaluminium was 4.0 mmol/l; the concentration of n-propyltrimethoxysilane was 0.2 mmol/l.

Data on the catalyst performance at the propylene polymerization are presented in Tables 1 and 2. In Tables 1 and 2 herein, "ME" means monoester.

Example 1a

Example 1a was carried out in the same way as Example 1, but in step E no n-propyltrimethoxysilane was used.

Example 2

A. Grignard Formation Step

A stirred flask, fitted with a reflux condenser and a funnel, was filled with magnesium powder (24.3 g). The flask was brought under nitrogen. The magnesium was heated at 80° C. for 1 hour, after which dibutyl ether (150 ml), iodine (0.03 g) and n-chlorobutane (4 ml) were successively added. After the colour of the iodine had disappeared, the temperature was raised to 80° C. and a mixture of n-chlorobutane (110 ml) and dibutyl ether (750 ml) was slowly added for 2.5 hours. The reaction mixture was stirred for another 3 hours at 80° C. Then the stirring and heating were stopped and the small amount of solid material was allowed to settle for 24 hours. By decanting the colorless solution above the precipitate, a solution of butylmagnesiumchloride (reaction product of step A) with a concentration of 1.0 mol Mg/l was obtained.

B. Preparation of the First Intermediate Reaction Product

This step was carried out as step B described in Example 1, except that the solution of reaction product of step A of Example 2 (360 ml, 0.36 mol Mg) and 180 ml of a solution of tetraethoxysilane (TES) in dibutyl ether (38 ml of TES and 142 ml of DBE), were used. As a result, a white solid reaction product of step B (the first intermediate reaction product; the support), was obtained, suspended in 200 ml of heptane. The average particle size of support was 20 μm and span value $(d_{90}-d_{10})/d_{50}=0.65$.

C. Preparation of the Second Intermediate Reaction Product

In inert nitrogen atmosphere at 20° C. a 250 ml glass flask equipped with a mechanical agitator is filled with slurry of 5 g of the first intermediate reaction product (see above step B of Example 2) dispersed in 60 ml of heptane. Subsequently a solution of 0.86 ml methanol (MeOH/Mg=0.5 mol) in 20 ml heptane is dosed under stirring during 1 hour. After keeping the reaction mixture at 20° C. for 30 minutes the slurry was slowly allowed to warm up to 30° C. for 30 min and kept at that temperature for another 2 hours. Finally the supernatant liquid is decanted from the solid reaction product (the second intermediate reaction product; activated support) which was washed once with 90 ml of heptane at 30° C.

D. Preparation of the Catalyst Component

This step was carried out as step D described in Example 1, except that 5.3 g of the above activated support, 0.937 g of ethyl acetate (EA/Mg=0.25 molar ratio) and 0.541 g of 9,9-bis-methoxymethyl-fluorene (flu/Mg=0.05 molar ratio) were used.

E. Polymerization of Propylene

This step was carried out as step E described in Example 1.

Example 2a

Example 2a was carried out in the same way as Example 2, but in step E no n-propyltrimethoxysilane was used.

Example 3

Example 3 was carried out in the same way as Example 2, but flu/Mg=0.1 molar ratio was used in step D instead of flu/Mg=0.05 molar ratio.

Example 3a

Example 3a was carried out in the same way as Example 3, but in step E no n-propyltrimethoxysilane was used.

Example 4

Example 4 was carried out in the same way as Example 3, but ethylbenzoate (EB/Mg=0.15 molar ratio) and 100° C. at stages I and II were used in step D instead of EA/Mg=0.25 molar ratio and 90° C.

Example 4a

Example 4a was carried out in the same way as Example 4, but in step E no n-propyltrimethoxysilane was used.

Example 5

Example 5 was carried out in the same way as Example 2, but the preparation of the catalyst component in step D was performed as follows.

A reactor was brought under nitrogen and 62.5 ml of titanium tetrachloride was added to it. The reactor was heated to 90° C. and a suspension, containing about 5.3 g of activated support in 15 ml of heptane, was added to it under stirring. Then the reaction mixture was kept at 90° C. for 10 min, and 0.937 g of ethyl benzoate (EA/Mg=0.25 molar ratio) in 2 ml of chlorobenzene was added to reactor. The reaction mixture was kept at 90° C. for 10 min, and 62.5 ml of chlorobenzene was added to reactor. The reaction mixture was kept at 90° C. for 30 min, and 1.082 g of 9,9-bis-methoxymethyl-fluorene (flu/Mg=0.1 molar ratio) in 3 ml of chlorobenzene was added to reactor. Temperature of reaction mixture was increased to 115° C. and the reaction mixture was kept at 115° C. for 60 min (stage I of catalyst preparation). Then the stirring was stopped and the solid substance was allowed to settle. The supernatant was removed by decanting, after which the solid product was washed with chlorobenzene (125 ml) at 100-110° C. for 20 min. Then the washing solution was removed by decanting, after which a mixture of titanium tetrachloride (62.5 ml) and chlorobenzene (62.5 ml) was added. The reaction mixture was kept at 115° C. for 30 min (stage II of catalyst preparation), after which the solid substance was allowed to settle. The supernatant was removed by decanting, and the last treatment was repeated once again (stage III of catalyst preparation). The solid substance obtained was washed five times using 150 ml of heptane at 60° C., after which the catalyst component, suspended in heptane, was obtained.

Example 5a

Example 5a was carried out in the same way as Example 5, but in step E no n-propyltrimethoxysilane was used.

Example 6

Example 6 was carried out in the same way as Example 5, but in step D ethylbenzoate (EB/Mg=0.15 molar ratio) at 100° C. instead of EA was used.

Example 6a

Example 6a was carried out in the same way as Example 6, but in step E no n-propyltrimethoxysilane was used.

Example CE1 (Comparative Experiment 1)

Example CE1 was carried out in the same way as Example 1, but the preparation of the catalyst component in step D was performed as follows.

A reactor was brought under nitrogen and 125 ml of titanium tetrachloride was added to it. The reactor was heated to 100° C. and a suspension, containing about 5.5 g of activated support in 15 ml of heptane, was added to it under stirring. Then the temperature of reaction mixture was increased to 110° C. for 10 min and 1.5 g of 9,9-bis-methoxymethyl-fluorene (flu) (flu/Mg=0.15 molar ratio) in 3 ml of chlorobenzene was added to reactor. Temperature of reaction mixture was increased to 115° C. and the reaction mixture was kept at 115° C. for 105 min (stage I of catalyst preparation). Then the stirring was stopped and the solid substance was allowed to settle. The supernatant was removed by decanting, after which the solid product was washed with chlorobenzene (125 ml) at 100-110° C. for 20 min. Then the washing solution was removed by decanting, after which a mixture of titanium tetrachloride (62.5 ml) and chlorobenzene (62.5 ml) was added. The reaction mixture was kept at 115° C. for 30 min (stage II of catalyst preparation), after which the solid substance was allowed to settle. The supernatant was removed by decanting, and the last treatment was repeated once again (stage III of catalyst preparation). The solid substance obtained was washed five times using 150 ml of heptane at 60° C., after which the catalyst component, suspended in heptane, was obtained.

Example CE1a (Comparative Experiment 1a)

Example CE1a was carried out in the same way as Example CE1, but in step E no n-propyltrimethoxysilane was used.

Example CE2 (Comparative Experiment 2)

Example CE2 was carried out in the same way as Example CE1, but EA/Mg=0.25 molar ratio and 90° C. was used in step D at I stage instead of flu/Mg=0.16 molar ratio and 115° C.

Example CE3 (Comparative Experiment 3)

Example CE3 was carried out in the same way as Example 2, but step D was performed without monoester at same conditions as in Example CE1 (flu/Mg=0.15 molar ratio).

Example CE3a (Comparative Experiment 3a)

Example CE3a was carried out in the same way as Example CE3, but in step E no n-propyltrimethoxysilane was used.

Example CE4 (Comparative Experiment 4)

Example CE4 was carried out in the same way as Example CE1, but EB/Mg=0.15 molar ratio and 100° C. were used in step D at stage I instead of flu/Mg=0.16 molar ratio and 115° C.

Example 6c

Example 6c was carried out in the same way as Example 2, but stage II in step D was performed with flu/Mg=0.04 mol at 115° C., di-n-butylphthalate (DBP) at DBP/Mg=0.1 molar ratio was used in stage III.

Example 6d

Example 6d was carried out in the same way as Example 6c, but in step E no n-propyltrimethoxysilane was used.

Example CE5 (Comparative Experiment 5)

Example CE5 was carried out in the same way as Example VIII of EP 2027164B1 under conditions of Example CE1, but in step D di-n-butylphthalate (DBP) as in EP2027164B1 was used at DBP/Mg=0.15 molar ratio instead of flu/Mg=0.15 molar ratio.

Example 7

Example 7 was carried out in the same way as Example, but in step D stage I was performed with EA/Mg=0.15 molar ratio, stage II was performed with flu/Mg=0.04 mol at 115° C., and stage III with di-n-butylphthalate (DBP) at DBP/Mg=0.05 molar ratio.

Example 7a

Example 7a was carried out in the same way as Example 7, but in step E no n-propyltrimethoxysilane was used.

Example 8

Example 8 was carried out in the same way as Example 7, but EB/Mg=0.15 molar ratio at 100° C. and flu/Mg=0.03 molar ratio were used in step D instead of EA/Mg=0.15 and flu/Mg=0.04 molar ratios respectively.

Example 8a

Example 8a was carried out in the same way as Example 8, but in step E no n-propyltrimethoxysilane was used.

Example 9

Example 9 was carried out in the same way as Example 8, but flu/Mg=0.04 and DBP/Mg=0.1 molar ratios were used in step D instead of flu/Mg=0.03 and DBP/Mg=0.05 molar ratios.

Example 9a

Example 9a was carried out in the same way as Example 9, but in step E no n-propyltrimethoxysilane was used.

TABLE 1

| Ex. | 1,3-diether/Mg | ME/Mg | 1,3-diether, wt % | ME Wt % | Ti, wt % | PP yield, kg/g cat. | APP, wt % | XS, % | MFR, dg/min | Mw/Mn |
|---|---|---|---|---|---|---|---|---|---|---|
| 1 | 0.05 | 0.25 (EA) | 13.7 | 3.3 | 2.9 | 12.0 | 0.53 | 3.0 | 13.3 | 3.8 |
| 1a | 0.05 | 0.25 (EA) | 13.7 | 3.3 | 2.9 | 19.4 | 0.78 | 5.8 | 40.3 | 4.3 |
| 2 | 0.05 | 0.25 (EA) | 9.7 | n.d. | 3.2 | 8.7 | 0.43 | 4.6 | 18.1 | 5.6 |
| 2a | 0.05 | 0.25 (EA) | 9.7 | n.d. | 3.2 | 15.3 | 3.2 | 10.9 | 45.8 | 4.9 |
| 3 | 0.1 | 0.25 (EA) | 12.0 | n.d. | 2.7 | 6.4 | 0.6 | 3.8 | 20.2 | 5.9 |
| 3a | 0.1 | 0.25 (EA) | 12.0 | n.d. | 2.7 | 11.0 | 1.0 | 7.0 | 30.0 | 5.1 |
| 4 | 0.1 | 0.15 (EB) | 11.8 | 3.6 | 2.8 | 5.4 | 0.9 | 4.6 | 15.6 | 5.9 |
| 4a | 0.1 | 0.15 (EB) | 11.8 | 3.6 | 2.8 | 7.3 | 1.0 | 7.3 | 32.2 | 5.2 |

TABLE 1-continued

| Ex. | 1,3-diether/Mg | ME/Mg | 1,3-diether, wt % | ME Wt % | Ti, wt % | PP yield, kg/g cat. | APP, wt % | XS, % | MFR, dg/min | Mw/Mn |
|---|---|---|---|---|---|---|---|---|---|---|
| 5 | 0.1 | 0.25 (EA) | 7.6 | n.d. | 3.1 | 7.2 | 1.0 | 6.4 | 17.6 | 5.6 |
| 5a | 0.1 | 0.25 (EA) | 7.6 | n.d. | 3.1 | 12.1 | 4.0 | 10.5 | 48.3 | 5.0 |
| 6 | 0.1 | 0.15 (EB) | 8.9 | 2.7 | 2.9 | 9.1 | 1.0 | 6.0 | 19.2 | 5.7 |
| 6a | 0.1 | 0.15 (EB) | 8.9 | 2.7 | 2.9 | 17.4 | 3.1 | 11.0 | 57.7 | 5.1 |
| CE1 | 0.15 | 0 | 16.5 | 0 | 3.4 | 9.2 | 0.8 | 3.5 | 10.7 | 5.1 |
| CE1a | 0.15 | 0 | 16.5 | 0 | 3.4 | 13.6 | 1.2 | 4.3 | 21.8 | 4.6 |
| CE2 | 0 | 0.25 (EA) | 0 | n.d. | 3.8 | 5.3 | 7.3 | 10.8 | 19.2 | 5.1 |
| CE3 | 0.15 | 0 | 12.7 | 0 | 2.8 | 4.2 | 1.0 | 4.5 | 8.7 | 6.2 |
| CE3a | 0.15 | 0 | 12.7 | 0 | 2.8 | 6.3 | 1.3 | 7.1 | 12.4 | 5.3 |
| CE4 | 0 | 0.15 (EB) | 0 | n.d. | 2.6 | 5.3 | 7.1 | 12.0 | 22.6 | 5.8 |

TABLE 2

| Ex. | 1,3-diether/Mg | DBP/Mg | ME/Mg | 1,3-diether wt % | ME Wt. % | DAP wt % | Ti wt % | PP yield kg/g cat | APP wt % | XS % | MFR dg/min | Mw/Mn |
|---|---|---|---|---|---|---|---|---|---|---|---|---|
| 7 | 0.03 | 0.05 | 0.15 (EA) | 5.5 | n.d. | 7.8 | 2.9 | 9.4 | 0.57 | 3.4 | 14.5 | 4.8 |
| 7a | 0.03 | 0.05 | 0.15 (EA) | 5.5 | n.d. | 7.8 | 2.9 | 10.7 | 1.9 | 0.2 | 43.9 | 4.9 |
| 8 | 0.03 | 0.05 | 0.15 (EB) | 5.2 | 1.3 | 7.6 | 2.3 | 11.0 | 0.52 | 3.6 | 16.2 | 4.4 |
| 8a | 0.03 | 0.05 | 0.15 (EB) | 5.2 | 1.3 | 7.6 | 2.3 | 12.5 | 2.5 | 5.3 | 46.1 | 4.3 |
| 9 | 0.04 | 0.1 | 0.15 (EB) | 5.8 | 0.8 | 9.5 | 2.0 | 9.7 | 0.4 | 2.0 | 14.6 | 4.6 |
| 9a | 0.04 | 0.1 | 0.15 (EB) | 5.8 | 0.8 | 9.5 | 2.0 | 10.5 | 1.7 | 8.9 | 52.8 | 4.3 |
| CE5 | 0 | | 0.15 | 0 | 0 | 10.5 | 2.6 | 13.5 | 0.5 | 3.0 | 12.7 | 4.8 |

Abbreviations and Measuring Methods

PP yield, kg/g cat is the amount of polypropylene obtained per gram of catalyst component.

APP, wt % is the weight percentage of atactic polypropylene. Atactic PP is the PP fraction soluble in heptane during polymerization. APP was determined as follows: 100 ml of the filtrate (y ml) obtained in separating the polypropylene powder (x g) and the heptane was dried over a steam bath and then under vacuum at 60° C. That yielded z g of atactic PP. The total amount of Atactic PP (q g) is: (y/100)*z. The weight percentage of Atactic PP is: (q/(q+x))*100%.

XS, wt % is xylene solubles, measured according to ASTM D 5492-10.

MFR is the melt flow rate as measured at 230° C. with 2.16 kg load, measured according to ISO 1133.

Mw/Mn: Polymer molecular weight and its distribution (MWD) were determined by Waters 150C gel permeation chromatograph combined with a Viscotek 100 differential viscosimeter. The chromatograms were run at 140° C. using 1,2,4-trichlorobenzene as a solvent with a flow rate of 1 ml/min. The refractive index detector was used to collect the signal for molecular weights.

Conclusions from the Experimental Data

In order to determine the effect of the combination of a monoester activator and a 1,3-diether internal donor, Example 1 can be compared to Comparative Example 1; Example 1a can be compared to Comparative Example 1a; Examples 2 and 3 can be compared to Comparative Example 3 and Examples 2a and 3a can be compared to Comparative Example 3a.

Ex. 1 compared to Ex. CE1 (no monoester) shows an increase of hydrogen sensitivity because the MFR values are higher by 24% (from 10.7 to 13.3 dg/min). Also an increase of catalyst activity is observed (from 9.2 to 12.0 kg PP yield per gram of catalyst) and it was observed that less internal donor was required, viz. 3 times lower amount of used 1,3-diether.

Ex. 1a compared to Ex. CE1a (no monoester) shows an increase of hydrogen sensitivity because the MFR values are higher by 85% (from 21.8 to 40.3 dg/min). Also an increase of catalyst activity is observed (from 13.5 to 19.4 kg PP yield per gram of catalyst) and it was observed that less internal donor was required, viz. 3 times lower amount of used 1,3-diether.

Ex. 2 and 3 compared to Ex. CE3 (no monoester) show: i) an increase of hydrogen sensitivity because the MFR values are higher by 2.1 (Ex. 2) or even 2.3 (Ex. 3) times; ii) an significant increase of catalyst activity from 4.2 to 8.7 (Ex. 2) or 6.4 (Ex. 3); iii) a lower amount (in 2-3 times) of used 1,3-diether (from 0.15 to 0.05 (Ex. 2) or 0.1 (Ex. 3).

Ex. 2a and 3a compared to Ex. CE3a (no monoester) show: i) an increase of hydrogen sensitivity because the MFR values are higher by 2.4 (Ex. 2a) or even 3.7 (Ex. 3a)

times; ii) an significant increase of catalyst activity from 6.3 to 15.3 (Ex. 2) or 11.0 (Ex. 3); iii) a lower amount (in 2-3 times) of used 1,3-diether (from 0.15 to 0.05 (Ex. 2) or 0.1 (Ex. 3).

In order to determine the effect of the combination of a monoester and a 1,3-diether internal donor also comparative tests (Comparative Examples 2 and 4) have been done wherein no 1,3-diether internal donor is present. Example 3 can be compared to Comparative Example 2; Example 4 can be compared to Comparative Example 4.

Ex. 3 compared to Ex. CE2 (no 1,3-diether) show: an increase in yield from 5.3 to 6.4, a significant decrease in XS wt. % from 10.8 to 3.8 and a significant decrease in APP wt. % from 7.3 to 0.6.

Ex. 4 compared to Ex. CE4 (no 1,3-diether) show: a similar yield 5.3 and 5.4, a significant decrease in XS wt. % from 12.0 to 4.6 and a significant decrease in APP wt. % from 7.1 to 0.9.

In order to determine the effect of the type of monoester Example 4 using ethylbenzoate as monoester can be compared to Example 3 using ethylacetate as monoester Ex. 4 (EB as monoester) compared to Ex. 3 (EA as monoester) shows similar hydrogen sensitivity and APP/XS values at lower catalyst activity;

In order to determine the effect of the moment of addition of the 1,3-diether with respect to the monoester Examples 5 and 6 can be compared to Example 3.

Ex. 5 and Ex. 6 (EB as monoester) are performed as Ex. 3 but 1,3-diether is introduced after monoester at stage I instead of stage III. Ex. 5 and Ex. 6 show that hydrogen sensitivity and catalyst activity are higher than that in Ex. CE3 (no monoester) and similar or higher to that in Ex. 3.

In order to determine the effect of the presence of an additional internal donors Examples 7-9 have been carried out.

Ex. 7-9 are performed using EA or EB as monoester and two internal donors (1,3-diether and DBP) and show high hydrogen sensitivity which is similar or higher to that in Ex. 1 (using EA and 1,3-diether) and significantly higher than that in Ex. CE1 (using only 1,3-diether without monoester) or Ex. CE5 (using only DBP).

From the above examples it can thus be concluded that the key to the present invention is the very specific combination of a monoester—as activator—and a 1,3-diether (e.g. a fluorene) as internal donor. This inventive combination of activator and internal donor leads to a higher yield and a higher melt flow rate, while the molecular weight distribution remains the same or even improves.

The invention claimed is:

1. A catalyst component manufactured by a process comprising:
   contacting a compound $R^9_z MgX_{2-z}$ wherein $R^9$ is an aromatic, aliphatic or cyclo-aliphatic group containing up to 20 carbon atoms, X is a halide, and z is in a range of larger than 0 and smaller than 2, with an alkoxy- or aryloxy-containing silane compound to give a first intermediate reaction product;
   contacting the first intermediate reaction product with at least one activating compound selected from the group of electron donors, compounds of formula $M(OR^{10})_{v-w}(OR^{11})_w$ wherein M is Ti, Zr, Hf, Al or Si, and $M(OR^{10})_{v-w}(R^{11})_w$ wherein M is Si, and each $R^{10}$ and $R^{11}$, independently, represent an alkyl, alkenyl or aryl group, v is the valency of M, v is 3 or 4, and w is less than v; to give a second intermediate reaction product; and
   contacting the second intermediate reaction product with a halogen-containing Ti-compound, a monoester as activating agent, a 1,3-diether as an internal electron donor, and optionally a diester as an additional internal electron donor.

2. A catalyst system for polymerization of olefins comprising the catalyst component according to claim 1, a co-catalyst and optionally an external electron donor.

3. The catalyst system according to claim 2, wherein no external donor is present.

4. A process for making a polyolefin comprising contacting an olefin with the catalyst system according to claim 2.

5. The process of claim 4, wherein the olefin is propylene.

6. The catalyst component of claim 1, wherein the at least one activation compound is the compound of formula $M(OR^{10})_{v-w}(R^{11})_w$ wherein M is Si.

7. The catalyst component of claim 1, wherein said monoester is present in an amount less than 4.0 wt. %.

8. The catalyst component of claim 1, wherein said monoester is present in an amount of up to 3.5 wt. %.

* * * * *

UNITED STATES PATENT AND TRADEMARK OFFICE
CERTIFICATE OF CORRECTION

PATENT NO. : 10,106,632 B2
APPLICATION NO. : 15/406124
DATED : October 23, 2018
INVENTOR(S) : Taftaf et al.

Page 1 of 1

It is certified that error appears in the above-identified patent and that said Letters Patent is hereby corrected as shown below:

Item (71) please correct the Applicant name to read as follows:
--SAUDI BASIC INDUSTRIES CORPORATION.--

Signed and Sealed this
Fourth Day of December, 2018

Andrei Iancu
*Director of the United States Patent and Trademark Office*